(12) United States Patent
Cao et al.

(10) Patent No.: US 11,716,942 B2
(45) Date of Patent: Aug. 8, 2023

(54) INFERIOR-ELIMINATING AND SUPERIOR-SELECTING BREEDING METHOD FOR SYNERGISTICALLY IMPROVING WHEAT YIELD AND QUALITY

(71) Applicant: Crop Research Institute, Shandong Academy of Agricultural Sciences, Shandong (CN)

(72) Inventors: Xinyou Cao, Shandong (CN); Jianjun Liu, Shandong (CN); Haosheng Li, Shandong (CN); Dungong Cheng, Shandong (CN); Libin Wang, Shandong (CN); Canguo Wang, Shandong (CN); Jianmin Song, Shandong (CN); Aifeng Liu, Shandong (CN); Zhendong Zhao, Shandong (CN)

(73) Assignee: Crop Research Institute, Shandong Academy of Agricultural Sciences, Jinan (CN)

( * ) Notice: Subject to any disclaimer, the term of this patent is extended or adjusted under 35 U.S.C. 154(b) by 111 days.

(21) Appl. No.: 17/066,568

(22) Filed: Oct. 9, 2020

(65) Prior Publication Data

US 2021/0022303 A1    Jan. 28, 2021

Related U.S. Application Data

(63) Continuation of application No. PCT/CN2019/112083, filed on Oct. 21, 2019.

(30) Foreign Application Priority Data

Jul. 11, 2019  (CN) .......................... 201910623647.2

(51) Int. Cl.
    *A01H 1/02*   (2006.01)
    *A01G 22/20*  (2018.01)
    *A01C 1/00*   (2006.01)

(52) U.S. Cl.
    CPC ............... *A01H 1/02* (2013.01); *A01C 1/00* (2013.01); *A01G 22/20* (2018.02)

(58) Field of Classification Search
    None
    See application file for complete search history.

(56) References Cited

FOREIGN PATENT DOCUMENTS

CN        103773883   *   5/2014

OTHER PUBLICATIONS

Thorwarth et al . Plant Breeding (2018):137(3), pp. 326-337.*
Aktas et al. Turk J Agric for (2017)41:127-134.*
Bernacchi et al. Theor Appl Genet (1998) 97:381-397.*
Chen et al. Mol. Breeding (2016)36:118.*
Dong et al. Journal of Genetics and Genomics (2007)34(9):836-841.*
Triticum aestivum Glu-1Bx gene, cultivar Saumur d'Automne line B, Oct. 13, 2016, Genbank No. LT626208.1, available at: https://www.ncbi.nlm.nih.gov/nuccore/LT626208.1.
Triticum aestivum cultivar Shinchunaga high-molecular-weight glutenin subunit (Glu) gene, Glu-1Bx7 allele, complete cds, Genbank No. JF736013.1, Sep. 19, 2011, available at: https://www.ncbi.nlm.nih.gov/nuccore/JF736013.1.
Triticum aestivum cultivar Shinchunaga high-molecular-weight glutenin subunit (Glu) gene, Glu-1By8 allele, complete cds, Genbank No. JF736014.1, Sep. 19, 2011, available at: https://www.ncbi.nlm.nih.gov/nuccore/JF736014.1.
Aegilops tauschii HMW glutenin subunit (Glu) gene, Glu-1Dx5 allele, complete cds, Genbank No. AY804129.2, May 8, 2007, available at: https://www.ncbi.nlm.nih.gov/nuccore/AY804129.2.
Aegilops tauschii strain Double high molecular weight glutenin subunit 1Dy10.1t (Glu-1Dy10.1t) gene, complete cds, Genbank No. AY863056.1, Jan. 19, 2005, available at: https://www.ncbi.nim.nih.gov/nuccore/AY863056.1.
Jinchuan Jia et al., Comparison test of new varieties of high-quality wheat, China Seed Industry, 2003, p. 35, vol. 12.
Jun Ji et al., A method of extraction and separation of wheat gluten, Hereditas (Beijing), Jan. 2008, pp. 123-126, vol. 30, No. 1.
O. D. Anderson et al., The characterization and comparative analysis of high-molecular-weight glutenin genes from genomes A and B of a hexapioid bread wheat, Theoretical and Applied Genetics, 1989, pp. 689-700, vol. 77.
Z.S. Lei et al., Y-type gene specific markers for enhanced discrimination of high-molecular weight glutenin alleles at the Glu-B1 locus in hexapioid wheat, Journal of Cereal Science, 2006, pp. 94-101, vol. 43, No. 1.
Hong Zhang et al., Characterization of Wheat Stripe Rust Resistance Genes in Shaanmai 139, ACTA Agronomica Sinica, 2010, pp. 109-114, vol. 36, No. 1.
Rules for Resistance Evaluation of Wheat to Diseases and Insect Pests, Part1: Rule for Resistance Evaluation of Wheat to Yellow Rust (*Puccinia striiformis* West. f. sp. *tritici* Eriks, *et Henn.*), Agricultural Industry Standard of the People's Republic of China, Sep. 14, 2007, pp. 1-14, NYT 1443.1-2007.

(Continued)

*Primary Examiner* — Medina A Ibrahim

(57) ABSTRACT

The present invention discloses an "inferior-eliminating and superior-selecting" breeding method for synergistically improving wheat yield and quality. A method for breeding target wheat varieties with improved yield and quality is provided herein, which combines the advantages of pedigree method and hybrid method, and provides a method for selection of all generations using molecular marker in combination with phenotype identification, and for selection of each generation according to different standards. Different from the derivative system method, the method reserves the traceability of line history and genetic relationship and the characteristics of simple operation and abundant genetic diversity of the hybrid method. The parents have clear backgrounds before combination and the selection process is simple and easy to operate, with clear goal, especially for those with no breeding experiences, it is easy to master and provides technical support for the rapid breeding of new varieties of high-quality and high-yield wheat.

2 Claims, 4 Drawing Sheets

Specification includes a Sequence Listing.

(56) References Cited

OTHER PUBLICATIONS

Rules of field investigation and grading of damage to winter wheat, Agricultural industry standards of the People's Republic of China, Dec. 24, 2012, pp. 1-26, NY/T 2283.2-2012.

Rules for the investigation and forecast of Wheat powdery mildew (*Blumeria graminis* (DC.) Speer), Agricultural Industry Standard of the People's Republic of China, Dec. 30, 2002, pp. 1-8, NY/T613-2002.

Wheat flour-Physical characteristics of doughs-Determination of water absorption and rheological properties using a farinograph, Standard of the People's Republic of China, May 18, 2006, pp. 1-10, GB/T14614-2006, corresponding to ISO 5530-1:1997.

Wheat flour—Physical characteristics of doughs—Part 1: Determination of water absorption and rheological properties using a farinograph, International Standard, Dec. 15, 1997, pp. 1-13, ISO 5530-1:1997 (E).

\* cited by examiner 1 2 3 4 5 6 7 8 9 10 11 12 13 14

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
ttagcgctaa gtgccgtct                                                19

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
ttgtcctatt tgctgccctt                                               20

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
gcctagcaac cttcacaatc                                               20

<210> SEQ ID NO 4
<211> LENGTH: 19
<212> TYPE: DNA
<213> ORGANISM: Artificial sequence
<220> FEATURE:
<223> OTHER INFORMATION: Synthetic

<400> SEQUENCE: 4
gaaacctgct gcggacaag                                                19
```

INFERIOR-ELIMINATING AND SUPERIOR-SELECTING BREEDING METHOD FOR SYNERGISTICALLY IMPROVING WHEAT YIELD AND QUALITY

CROSS REFERENCE TO RELATED APPLICATION

The present application is a continuation application of PCT application No. PCT/CN2019/112083 filed on Oct. 21, 2019, which claims the benefit of Chinese Patent Application No. 201910623647.2 filed on Jul. 11, 2019. The contents of the above applications are incorporated herein by reference in their entirety.

REFERENCE TO SEQUENCE LISTING

The Sequence Listing is submitted as an ASCII formatted text file via EFS-Web, with a file name of "Sequence_Listing.txt", a creation date of Sep. 30, 2020, and a size of 1,108 bytes. The Sequence Listing filed via EFS-Web is part of the specification and is incorporated in its entirety by reference herein.

FIELD OF THE INVENTION

The present invention relates to general field of biotechnology, and specifically relates to an "inferior-eliminating and superior-selecting" breeding method for synergistically improving wheat yield and quality.

BACKGROUND

Wheat has always been the main food ration for the people in northern china. With the decreasing area of arable lands, increasing the yield per unit area has become the sole way to increase the total yield and guarantee the food security in china. With the improvement of people's living standards and changes in dietary structure, strategic adjustment should be made for the wheat production in china, switching from a simple yield type to a high-quality, high-yield and high-efficiency type. Since the yield and quality of wheat have always been recognized as contradictions, it is urgent to solve the relationship between them. Although Chinese breeders have proposed some indicators for selecting high-quality strong gluten wheat, they are basically partial improvements, without systematic reports for improving both quality and quantity.

Wheat is a conventional self-pollinated crop. At present, the pedigree method, hybrid method, derivative system method, single seed descend method and double haploid method are commonly used in the selection of hybrid progeny at home and abroad. In china, the pedigree method is the most widely used method. However, with the increase of labor costs and the continuous expansion of breeding scale, these methods are difficult to meet the current breeding needs.

SUMMARY

In order to breed target wheat varieties with high yield and improved quality, the present invention provides the following technical solutions.

The object of the present invention is to provide a method for breeding target wheat varieties with improved yield and quality.

The method comprises the following steps:

1) Selecting parental combinations that meet the following criterion from multiple parental combinations as multiple candidate parental combinations; and the criterion is that two parents in the parental combinations contain at least one high-quality related protein;

2) Hybridizing the multiple candidate parental combinations respectively to obtain $F_0$ hybrid grains; hand sowing the $F_0$ hybrid grains to obtain $F_1$ single-row populations; and then selecting a single plant with the yield per plant is greater than that of a high-quality control variety or greater than or equal to that of a high-yield control variety or is below 5% lower than a high-yield control variety from the $F_1$ single-row populations as a selected $F_1$ single plant;

3) Collecting all seeds of the selected $F_1$ single plants, choosing the seeds larger than 8-mesh sieve for plot sowing, to obtain $F_2$ plot populations; selecting plots that meet the following criteria 3)-1 to 3)-3 from the $F_2$ plot populations as selected $F_2$ plots;

3)-1, plots with the grade of stripe rust less than 4 and winter freezing injury less than grade 4; 3)-2, plots with the yield greater than that of a high-quality control variety or greater than or equal to that of a high-yield control variety or is below 5% lower than a high-yield control variety; 3)-3, plots with the TGW greater than or equal to 35 g;

4) Hand sowing the grains of the single plant in the selected $F_2$ plot to obtain $F_3$ populations; selecting single plants that meet the following criteria 4)-1 to 4)-3 from the $F_3$ populations, to obtain selected $F_3$ single plants;

4)-1, single plants containing high-quality-associated protein; 4)-2, single plants with no less than 5 tiller-earing, stick or square ears, flag leaves raised (appropriate with an angle between the flag leaves of 10-30 degrees), powdery mildew less than grade 4, stripe rust less than grade 4, and plant height of 70-85 cm; 4)-3, the protein content of single plant grains is greater than or equal to 13%;

5) Hand sowing the grains of the selected $F_3$ single plants to obtain F4 plant-to-row populations; selecting single plants that meet the following criteria 5)-1 to 5)-5 from the F4 plant-to-row populations, to obtain selected F4 plant-to-row;

5)-1, winter freezing injury is less than or equal to grade 3; 5)-2, both grade of powdery mildew and grade of stripe rust are less than 4; 5)-3, plant height is 75-80 cm; 5)-4, plant-to-row with TGW greater than or equal to 38 g; 5)-5, the peak time of the mixograph in the mixing characteristics identification of plant-to-row single plants is not less than 2 minutes, and the 8-minute band width is not less than 10%;

6) Simultaneously hand sowing and plot sowing the single plant seeds of F4 plant-to-row, to obtain F5 plant-to-row populations and F5 plot populations; selecting the single plants that meet both the selection criteria of plant-to-row populations and the plot selection criteria as the target wheat variety;

The plot selection criteria include the following 6)-1 to 6)-3:

6)-1, the winter freezing injury is less than or equal to grade 3, the number of ears per mu is greater than the high-quality control or equal to the high-yield control, and the lodging is less than or equal to grade 2;

6)-2, the dough stability time in the plot quality identification is not less than 8 minutes, and the bread score is not less than 80;

6)-3, the plot yield is greater than that of high-quality control variety or greater than or equal to that of high-yield control variety, or below 5% lower than the high-yield control variety;

The selection criteria of plant-to-row populations include the following 6)-4 to 6)-5:

6)-4, plant-to-rows with the yield greater than the high-quality control variety or greater than or equal to the high-yield control variety, or with the yield below 5% lower than the high-yield control variety;

6)-5, single plants containing high-quality-associated protein.

In the foregoing method, the target wheat variety with improved yield and quality has a yield and quality higher than the high-yield control or high-quality control.

The foregoing high-yield control is a high-yield regional trial control variety of the local wheat area, and it is specifically Jimai 22 in the embodiments of the present invention; the foregoing high-quality control is a high-quality regional trial control variety of the local wheat area, and it is specifically Jinan 17 in the embodiments of the present invention.

In the foregoing method, the plot sowing is sowing in strips;

or, the hand sowing is plant-to-row sowing.

In the foregoing method, in the step 1), the method for selecting parental combinations that meet the following criterion from multiple parental combinations: performing protein-level identification and molecular-level identification on multiple parental combinations, and selecting any parent in the combination that contains at least one high-quality-associated protein, and the cDNA of any parent in the combination containing the DNA molecule encoding the high-quality-associated protein;

or, single plants that contain high-quality-associated protein selected in the step 4) and step 6) have passed the molecular-level identification;

The protein-level identification is to detect the molecular weight of the high-quality-associated protein by SDS electrophoresis; the specific method is as follows: extract the total protein of sample, detect the molecular weight by electrophoresis, and obtain bands with a size of high-quality-associated protein, then the sample contains the high-quality-associated protein;

The molecular-level identification is to amplify the high-quality-associated protein with a molecular marker corresponding to the high-quality-associated protein.

The specific method is as follows: amplify samples to be tested using the molecular marker corresponding to the high-quality-associated protein, to obtain the size of PCR product corresponding to the molecular marker, then the samples to be tested contain DNA molecules encoding high-quality-associated protein, so as to determine that samples to be tested contain high-quality-associated protein.

In the foregoing method, the high-yield control is a high-yield regional trial control variety in a local wheat area;

Or, the high-quality control is a high-quality regional trial control variety in a local wheat area.

In the foregoing method, in the step 2), hand sowing the F0 hybrid grains is to carry out hand sowing of 40 grains of the $F_0$ hybrid grains in a row length of 2 to 4 meters;

in the step 3), the plot sowing is to sow 6 rows in a plot of 4 meters long and 1.5 meters wide;

in the step 4), the hand sowing is to sow 60 rows per ear and 80 grains per row;

in the step 5), the hand sowing is to sow 60 rows per ear and 80 grains per row.

In the foregoing method, the high-quality-associated protein is any one of glutenin subunit 11 (Genbank No: LT626208.1.2016.10.13), glutenin subunits 7+8 (Genbank No: JF736013.1.2011.9.19, JF736014.1.2011.9.19) and glutenin subunits 5+10 (Genbank No: AY804129.2.2007.3.8, AY863056.1.2005.1.19).

In the foregoing method, the molecular marker corresponding to the 7+8 HMW-GS is By8 molecular marker;

The molecular marker corresponding to the 5+10 HMW-GS is Dx5 molecular marker;

The By8 molecular marker is composed of single-stranded DNA molecule shown in SEQ ID NO: 1 or derivatives thereof and single-stranded DNA molecule shown in SEQ ID NO: 2 or derivatives thereof;

The Dx5 molecular marker is composed of single-stranded DNA molecule shown in SEQ ID NO: 3 or derivatives thereof and single-stranded DNA molecule shown in SEQ ID NO: 4 or derivatives thereof.

In the foregoing method, the single-stranded DNA molecule or derivative thereof is a single-stranded DNA molecule that has undergone one or several nucleotide substitutions and/or deletions and/or additions and has the same function as the single-stranded DNA molecule.

In the foregoing method, the parental combination is a combination of Ji 954072 and Jinan 17 or a combination of Ji 954072 and Jimai 19.

In the foregoing method, the yield of the plot is calculated according to the following method: first select single plants with the grade of stripe rust less than or equal to 1, the single ear length not less than 8 cm, the stick or square ears and the plant height of 70-85 cm from a selected plot and record them as single ear selected single plants, count the weights of grains of all single ear selected single plants in the plot, then harvest other single plant grains except the single ear selected single plants, and count their weights of grains; then calculate the yield of the plot by adding the weights of grains of single ear selected single plants with the weights of grains of other single plants;

In the foregoing method, the yield per plant of $F_1$ single-row populations is the yield of $F_1$ single-row populations/the number of $F_1$ grains sowed in a single row;

In the foregoing method, the protein content of the grains is determined by the DA7200 multifunctional near-infrared analyzer, to determine the grain quality.

The present invention combines the advantages of pedigree method and hybrid method, and provides a method for selection of all generations using molecular marker in combination with phenotype identification, and for selection of each generation according to different standards. Different from the derivative system method, it reserves the traceability of line history and genetic relationship and the characteristics of simple operation and abundant genetic diversity of the hybrid method. The parents have clear backgrounds before combination and the selection process is simple and easy to operate, with clear goal, especially for those with no breeding experiences, it is easy to master and provides technical support for the rapid breeding of new varieties of high-quality and high-yield wheat.

DETAILED DESCRIPTION

The experimental methods used in the following examples are conventional methods unless otherwise specified.

The materials and reagents used in the following examples are commercially available unless otherwise specified.

Test materials: Ji 954072, Jinan 17, Jimai 19 and other parent materials.

Ji 954072 (Jia Jinchuan, Xu Shiqing, Sun Yan, Pan Meichang, Xu Haiyang. Comparison test of new varieties of high-quality wheat [J]. China Seed Industry, 2003, (12):35);

Jinan 17 is sold by Shandong Luyan Agricultural Co., Ltd.; Jimai 19 is sold by Shandong Luyan Agricultural Co., Ltd.

Example 1 A Wheat Breeding Method for Improving Yield and Quality

Two combination ways were used as an example below.
Combination 1: Combination of Ji 954072 and Jinan 17
Combination 2: Combination of Ji 954072 and Jimai 19.
I. A wheat breeding method for improving yield and quality 1. Identifying the Presence of Proteins Related to Yield or Quality in the Parental Combination 1) Detection at Protein Level
The glutenins were extracted from Ji 954072, Jinan 17, and Jimai 19 respectively (Ji Jun, Liu Dongcheng, Wang Jing, et al. A method for extracting wheat high and low molecular weight glutenin subunits [J]. Heredity, 2008, 30(1): 123-126.), and detected by SDS-PAGE.

Chuanmai 56 and Zhongguochun were used as standard controls.

Figure 1:
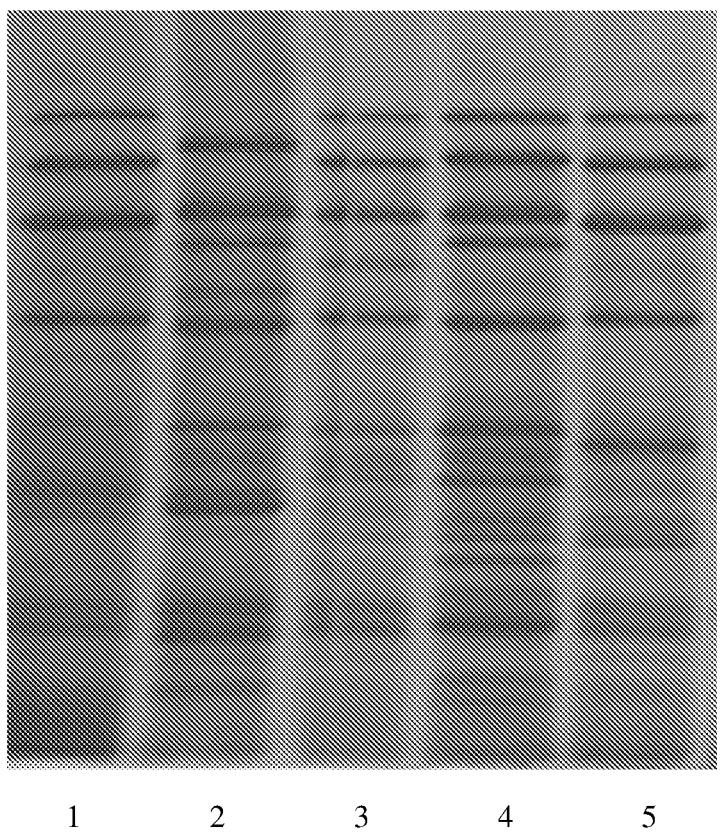
FIG. 1 shows the SDS-PAGE electrophoresis pattern of HMW-GS, from left to right: lane 1: Chuanmai 56 (standard control); lane 2: Zhongguochun (standard control) lane 3: Shumai 482 (standard control); lane 4: Jinan 17; lane 5: Ji 954072.

The SDS-PAGE electrophoresis patterns of HMW-GS of Ji 954072, Jinan 17, and Jimai 19 were shown in FIG. 1, from left to right: lane 1: Chuanmai 56 (standard control); lane 2: Zhongguochun (standard control) lane 3: Shumai 482 (standard control); lane 4: Jinan 17; lane 5: Ji 954072, in which Ji 954072 contains 1, 7+9, 5+10 HMW-GS; Jinan 17 contains 1, 7+8, 4+12 HMW-GS; and Jimai 19 contains 1, 7+8, 2+12 HMW-GS.

Among them, glutenin subunits related to high quality were 1 (Genbank No: LT626208.1. 2016.10.13), 7+8 (Genbank No: JF736013.1.2011.9.19), JF736014.1.2011.9.19) and 5+10. (Genbank No: AY804129.2.2007.3.8, AY863056.1.2005.1.19).

Ji 954072, Jinan 17 and Jimai 19 all contained 2 glutenin subunits related to high quality. To cultivate the wheat with better quality, three glutenin subunits related to high quality were required, namely, 1, 7+8, 5+10 HMW-GS.

2) Detection at Molecular Level
The genomic DNA of the leaf tissues of Ji 954072, Jinan 17 and Jimai 19 were extracted, respectively. PCR amplification was performed using Dx5 molecular marker of 5+10 HMW-GS and the By8 molecular marker of 7+8 HMW-GS in Table 1.

TABLE 1

Information of Dx5 and By8 molecular markers and amplification conditions

| Allele | Marker name | Primer sequence (5'-3') | Annealing temperature | Amplified fragments | References |
|---|---|---|---|---|---|
| Dx5 | Dx5 | Forward: GCCTAGCAACCTTCACAATC (SEQ ID NO: 3) Reverse: GAAACCTGCTGCGGACAAG (SEQ ID NO: 4) | 63° C. | 450 bp | Anderson et al, 1989 |
| By8 | ZSBy8F5/R5 (By8) | Forward: TTAGCGCTAAGTGCCGTCT (SEQ ID NO: 1) Reverse: TTGTCCTATTTGCTGCCCTT (SEQ ID NO: 2) | 64° C. | 527 bp | Lei et al, 2006 |

Figure 2:
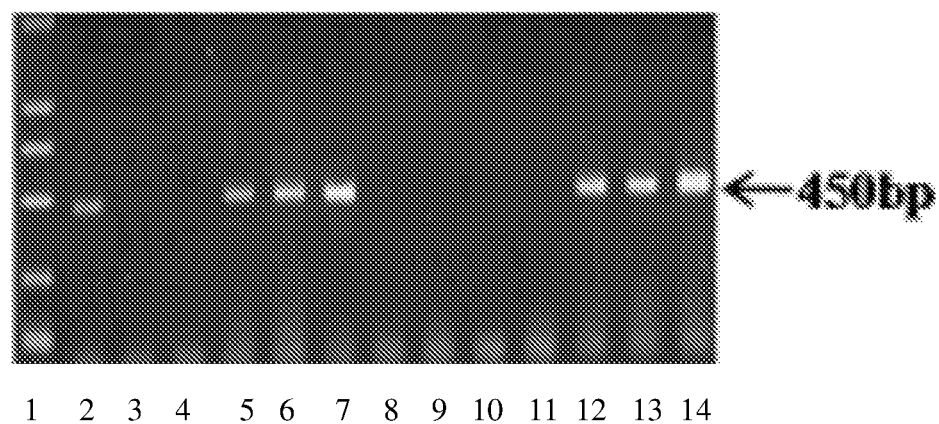
FIG. 2 shows the molecular marker detection of Dx5 subunit; from left to right: lane 1: Marker; lane 2: Ji 954072; lane 3: Jinan 17; lane 4: Jimai 19; lanes 5-14: other varieties.

The amplification result of Dx5 molecular marker was shown in FIG. 2, from left to right: lane 1: Marker; lane 2: Ji 954072; lane 3: Jinan 17; lane 4: Jimai 19; lanes 5-14: other varieties. As shown from the figure, 450 bp was amplified for Ji 954072, i.e. containing 5+10 HMW-GS encoding DNA molecules; while no target fragments were obtained for Jinan 17 and Jimai 19 after Dx5 amplification.

Figure 3:
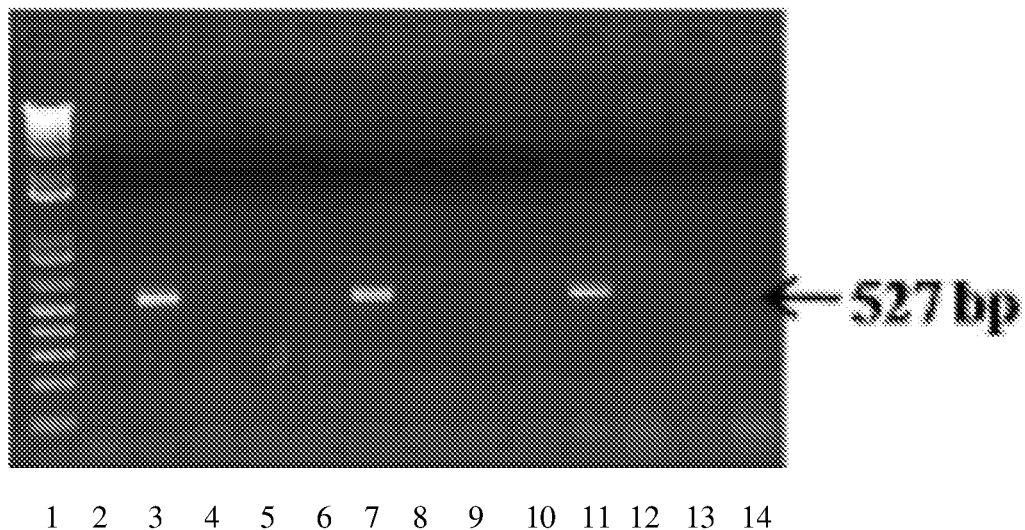
FIG. 3 shows the molecular marker detection of By8 subunit; from left to right: lane 1: Marker; lane 2: Ji 954072; lane 3: Jinan 17; lanes 4-6: other varieties; lane 7: Jimai 19; lanes 814: other varieties.

The amplification result of By8 molecular marker was shown in FIG. 3, from left to right: lane 1: Marker; lane 2: Ji 954072; lane 3: Jinan 17; lanes 4-6: other varieties; lane 7: Jimai 19; lanes 8-14: other varieties. As shown from the figure, 527 bp was amplified for Jinan 17, i.e. containing 7+8 HMW-GS; and 527 bp was amplified for Jimai 19, i.e. containing 7+8 HMW-GS; while no target fragments were obtained for Ji 954072 after By8 amplification.

The results were consistent with the SDS-PAGE results. The two markers could also be used for progeny molecular marker assisted selection and detection described below.

Therefore, the combination of Ji 954072 and Jinan 17, and the combination of Ji 954072 and Jimai 19 were expected to breed single plants with 1, 7+8, and 5+10 HMW-GS combinations, that is, the 5+10 HMW-GS in Ji 954072 was transferred to Jinan 17 and Jimai 19 respectively to substitute 4+12 and 2+12 subunits.

2. Obtaining Hybrid F1 Generation and Breeding the Selected Combinations

1) Obtaining Hybrid F1 Generation by Hand Sowing and Breeding the Following F1 Single Plants 1) Hand Sowing Obtains Hybrid F1 Generation and Selects the Following F1 Single Plant The female parent Ji 954072 and the male parent Jinan 17 were hybridized to obtain F0 hybrid grains.

Four hybrid ears were made for each combination of Ji 954072 and Jinan 17.

The number of hybrid grains harvested was counted, and if the number of hybrid grains was less than 40 or the grains were too deflated, they would be eliminated.

All of the above 40 $F_0$ hybrid grains were hand sowed (1 grain at 5 cm) according to the row length of 2 meters, to obtain F1 single-row populations of Ji 954072 and Jinan 17 combination.

The female parent Ji 954072 and the male parent Jimai 19 were hybridized to obtain $F_0$ hybrid grains.

Four hybrid ears were made for each combination of Ji 954072 and Jimai 19.

The number of hybrid grains harvested was counted, and if the number of hybrid grains was less than 40 or the grains were too deflated, they would be eliminated.

All of the above 40 $F_0$ hybrid grains were hand sowed (1 grain at 5 cm) according to the row length of 2 meters, to obtain F1 single-row populations of Ji 954072 and Jimai 19 combination.

2) Selection of Hybrid F1 Generation for Yield Per Plant

The yield per plant of the $F_1$ single-row populations obtained in the above two combinations were calculated respectively, and $F_1$ single plants with the yield per plant was greater than the high-quality control variety (Jinan 17) or greater than or equal to the high-yield control variety (Jimai 22), or was below 5% lower than the high-yield control variety as a selected $F_1$ single plants.

The specific method:

After harvesting all the $F_1$ single-row populations obtained in the above two combinations, they were weighed and the yield per plant was calculated by the formula: yield per plant=single-row population yield/number of single-row seeds sowed. The results was that the $F_1$ yield per plant of Ji 954072/Jinan 17 combination was 11.3 grams, and the $F_1$ yield per plant of Ji 954072/Jimai 19 combination was 10.5 grams. Using 40 grains of high-yield control (high-yield regional trial control variety Jimai 22 for local wheat area) and 40 grains of high-quality control (high-quality regional trial control variety Jinan 17 for local wheat area) that were hand sowed according to a row length of 2 meters (1 grain at 5 cm) as the controls, the yield per plant of the controls was counted. Results showed that the yield per plant of the control variety Jimai 22 was 12.8 g, and the yield per plant of the control variety Jinan 17 was 10.2 g.

After comparison, the selected F1 single plants were obtained. The F1 generation from Ji 954072 and Jimai 14 and the F1 generation from Ji 954072 and Jinan 17 were selected.

3. Obtaining F2 Generation by Plot Sowing and Breading the Selected $F_2$ Plot

1) Obtaining $F_2$ Generation by Plot Sowing

Figure 4:
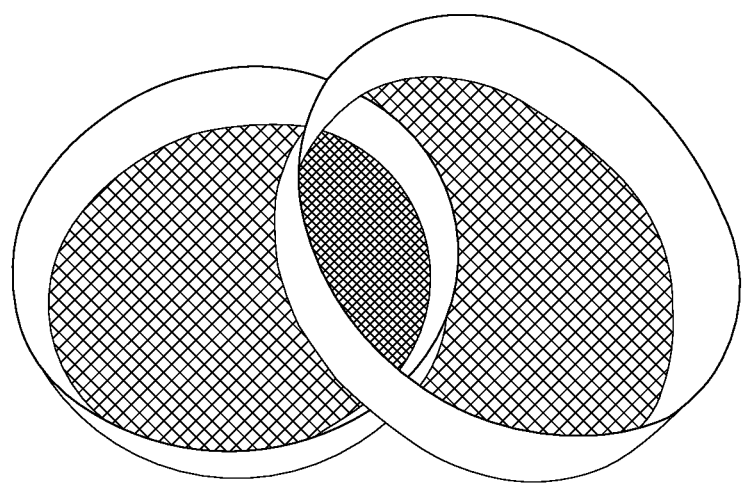
FIG. 4 shows an 8-mesh iron sieve.

The selected F1 single plant seeds from the above two combinations were sieved with 8-mesh sieves (as shown in FIG. 4) to obtain F1 single plant seeds larger than 8 meshes (the purpose was to remove the seeds with low TGW);

120 grams of F1 single plant seeds larger than 8 meshes from the two combinations were weighed for plot sowing, with the plot of 4 meters long, 1.5 meters wide, and 6 rows. Austrian plot sowing machine was used for sowing in strips, which was close to or higher than the production planting density, to obtain $F_2$ plot populations derived from the two combinations.

At the same time, the high-yield control wheat (Jimai 22) and high-quality control wheat (Jinan 17) were planted to obtain control Jimai 22 plot and control Jinan 17 plot.

2) $F_2$ Generation Selection

The plots that met the following criteria (1) to (3) were chosen from $F_2$ plot populations as the selected $F_2$ plots: (1) the plots with grade of stripe rust less than grade 4 and winter freezing injury less than grade 4; (2) the plots with yield greater than that of a high-quality control variety or greater than or equal to that of a high-yield control variety or is below 5% lower than a high-yield control variety; (3) the plots with TGW greater than or equal to 35 grams. The specific steps were as follows.

(1) Field Selection

A. Stripe Rust

Huixianhong wheat was planted around the F2 plot populations derived from two combinations (Zhang Hong, Ren Zhilong, Hu Yingang, et al. Genetic analysis of anti-stripe rust genes in Shaanmai 139 [J]. Acta Agronomica Sinica, 2010, 36(1): 109-114.). The stripe rust inoculation was carried out by sweeping method during the jointing stage. The specific method was as follows: Tween20 aqueous solution (0.05%, V/V) was used to spray leaves, to make mist droplets evenly distributed on the leaves, and then physiological strains CYR29 and CYR32 of the mixed stripe rust fungus were directly applied to inoculate.

Stripe rust was generally divided into the following grades (NY/T 1443.1-2007): "0" nearly immunity: completely asymptomatic, or occasionally very small light spots, various types of dead spots, no spore sorus; "1" high resistance: very few uredinium, with obvious dead spots around; "2" moderate resistance: few and scattered uredinium, with normal shape, chlorosis or dead spots around; "3" moderate infection: more uredinium, normal shape, with chlorosis around; "4" high infection: very more uredinium, no chlorosis around.

The $F_2$ plot populations derived from the combination of Ji 954072 and Jinan 17 had a stripe rust grade of 3;

The $F_2$ plot populations derived from the combination of Ji 954072 and Jimai 19 had a stripe rust grade of 3.

B. Winter Freezing Injury

The winter freezing injury grade of $F_2$ plot populations derived from the two combinations was observed. It was divided into five grades (National Standard NY/T 2283.2-2012). Grade "1": no frost damage; grade "2": yellow leaf tip by freezing; grade "3": half of leaves were frozen to death; grade "4": all leaves were completely withered; grade "5": plants were frozen to death.

The $F_2$ plot populations derived from the combination of Ji 954072 and Jinan 17 had a winter freezing injury grade of 3;

The $F_2$ plot populations derived from the combination of Ji 954072 and Jimai 19 had a winter freezing injury grade of 3.

The $F_2$ plot populations with winter freezing injury grade less than 4 and stripe rust grade less than 4 as the $F_2$ plot populations selected from the field.

Figure 5:
FIG. 5 shows a schematic diagram for ear selection by 3M tape.

(2) Selection of Plot Yield a, Selection of Single Ears $F_2$ plot populations derived from the two combinations in above 1) were used for single ear selection. The single plants with the grade of stripe rust less than or equal to 1, the single ear length not less than 8 cm, the stick or square ears and the plant height of 70-85 cm were selected and recoded as single ear selected single plants (3M blue labels were used to select ears, FIG. 5), and the weights of grains of all single ear selected single plants in the $F_2$ plot were counted.

b. Yield of Plots

The grains of single plants other than the single ear selected single plants in the $F_2$ plot were mechanically harvested.

The yield of $F_2$ plot was calculated according to the formula: yield of $F_2$ plot=weight of grains of all single ear selected single plants in the $F_2$ plot+weight of grains of single plants other than the single ear selected single plants in the $F_2$ plot.

The yield of the $F_2$ plot derived from the combination of Ji 954072 and Jinan 17 was 5.21 kg;

The yield of the $F_2$ plot derived from the combination of Ji 954072 and Jimai 19 was 4.79 kg;

The yields of the control Jimai 22 plot and the control Jinan 17 plot were calculated, which were 5.46 kg and 5.02 kg, respectively.

The $F_2$ plots with the yield greater than or equal to high-yield control wheat (Jimai 22) or high-quality control wheat (Jinan 17) were selected to obtain the selected $F_2$ plot populations for plot yield.

According to the above yield results, the results of $F_2$ plot derived from the combination of Ji 954072 and Jinan 17 were consistent, and reserved; the results of $F_2$ plot derived from the combination of Ji 954072 and Jimai 19 were not consistent and would be eliminated. The $F_2$ plot derived from the combination of Ji 954072 and Jinan 17 was used as the selected $F_2$ plot populations for plot yield.

(3) TGW

The TGW of $F_2$ plot populations derived from the two combinations was counted. The TGW of $F_2$ plot derived from the combination of Ji 954072 and Jinan 17 was 43 grams, and the TGW of $F_2$ plot derived from the combination of Ji 954072 and Jimai 19 was 42 grams.

The plots with TGW greater than or equal to 35 grams were recorded as selected $F_2$ plot populations for TGW.

The plots that met the foregoing (1), (2) and (3), that is, plots that met grade of stripe rust less than 4 and winter freezing injury less than 4, plots with yield greater than or equal to high-yield control varieties or high-quality control varieties, and plots with TGW greater than or equal to 35 grams were $F_2$ plots derived from the combination of Ji 954072 and Jinan 17; and they were recorded as selected $F_2$ plots;

4. Obtaining and Selecting of F3 Generation

1) Obtaining of F3 Generation

Figure 6:
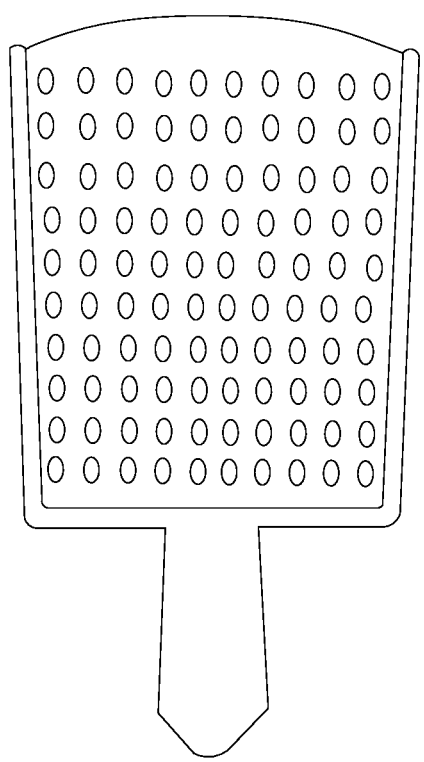
FIG. 6 shows 80 grains counted by a counting plate.

Single ears of all single plants selected in the F2 plot in the foregoing 3 were planted in the plots in the next year, 60 rows for single ears and 80 grains each row. Eighty grains were counted by a counting plate (FIG. 6), and Austrian hand sowing machine was used for hand sowing, to obtain F3 populations.

After sorting out, one row of high-yield control and one row of high-quality control were added for every 10 rows in each plot.

2) Selection of F3 Generation

Single plants that met the following criteria (1) to (3) were selected from the F3 populations to obtain the selected F3 single plants: (1) single plants containing high-quality-associated protein; (2) single plants with no less than 5 tiller-earing, stick or square ears, flag leaves raised (with an angle between the flag leaves of 10-30 degrees), powdery mildew less than grade 4, stripe rust less than grade 4, and plant height of 70-85 cm; (3) the protein content of single plant grains was greater than or equal to 13%; specifically:

(1) Selection of Single Plants Containing High-Quality-Associated Protein by Molecular Identification Before overwintering, the F3 populations were tagged and leaves of single plants were taken. DNA was extracted as a template by conventional methods. The Dx5 molecular marker (target fragment of 450 bp) and By8 molecular marker (target fragment of 527 bp) were used for detection respectively. The single plants containing Dx5 molecular marker target fragments and By8 molecular marker target fragments, namely, the single plants containing 1, 7+8, and 5+10 subunits, were recorded as selected single plants of F3 populations for molecular identification. A total of 382 plants were selected.

(2) Field Testing

The above selected single plants of F3 populations for molecular identification were chosen according to the following criteria. The single plants with no less than 5 tiller-earing, stick or square ears, flag leaves raised (with an angle between the flag leaves of 10-30 degrees), powdery mildew less than grade 4, stripe rust less than grade 4, and plant height of 70-85 cm were recorded as selected F3 single plant populations for field testing.

The national standard for grading of powdery mildew is NY/T613-2002. Generally the peak period of powdery mildew is the wheat earing stage, which is investigated and recorded by five grades. Grade "1" indicated no visible symptom on leaves; grade "2" indicated grassroots leaves were diseased; grade "3" indicated disease spots spread to the middle leaves; grade "4" indicated disease spots spread to flag leaves; grade "5" indicated disease spots spread to ears and awns; nationally occurring disease in the field adopted). A total of 275 plants were selected.

(3) Identification of Grain Quality

The grains of selected F3 single plants for field testing obtained in the above (2) were harvested, and grain quality was determined by a DA7200 multifunctional near-infrared analyzer according to the principle of "eliminating inferior" rather than "selecting superior". The judgment: F3 populations with the protein content of single plant grains greater than or equal to 13% were chosen as the selected grains of F3 single plants. A total of 156 plants were selected.

5. Obtaining of F4 Generation and Selection of Selected F4 Single Plants

1) Obtaining of F4 Generation

Eighty grains of selected F3 single plants obtained in the above 4 were counted by a counting plate, and planted in rows, with 4 meters long, and an Austrian hand sowing machine was used for hand sowing, to obtain F4 plant-to-row populations. One row of high-yield control and one row of high-quality control were added for every 10 rows.

2) Selection of F4 Generation

Single plants that met the following criteria (1) to (5) were selected from the F4 plant-to-row populations to obtain the selected F4 plant-to-rows.

(1) winter freezing injury was less than or equal to grade 3; (2) both grade of powdery mildew and grade of stripe rust were less than 4; (3) plant height of 75-80 cm; (4) plant-to-rows with TGW greater than or equal to 38 g; (5) The peak time of the mixograph in the mixing characteristics identification of plant-to-row single plants was not less than 2 minutes, and the 8-minute band width was not less than 10%. Details were described as follows:

(1) Investigation on Winter Freezing Injury Before Wintering

F4 plant-to-rows were selected from F4 plant-to-row population with grade of winter freezing injury less than or equal to 3 to obtain F4 plant-to-row populations for identification of winter freezing injury. A total of 227 plant-to-rows were selected.

(2) Disease Resistance

The F4 plant-to-row populations with the grade of powdery mildew and grade of stripe rust both less than 4 were chosen from F4 plant-to-rows for identification of winter freezing injury, to obtain F4 plant-to-row populations for disease resistance identification. A total of 169 plant-to-rows were selected.

(3) Field Traits

The plant-to-rows with plant height of 75-80 cm were chosen from F4 plant-to-row populations for disease resistance identification, to obtain the F4 plant-to-row populations for field trait identification. A total of 138 plant-to-rows were selected.

(4) TGW Identification

The F4 plant-to-row populations for field trait identification were tagged. The whole row was completely plucked and degranulated for each single plant. Eighty grains were reserved for a single plant, and other grains in the row were all mixed, to determine TGW. The plant-to-rows with TGW greater than or equal to 38 g were chosen and recorded as F4 plant-to-row populations for TGW identification. A total of 116 plant-to-rows were selected.

(5) Mixing Characteristics Identification 200 grams of grains were taken from F4 plant-to-row populations for TGW identification, and ground, then mixing characteristics was determined by a mixograph. The single plants with mixograph peak time not less than 2 minutes and 8-minute band width not less than 10% were selected.

The F4 population single plants that met the above selection criteria were the selected F4 single plants. A total of 55 plant-to-rows were selected.

6. Obtaining and Identification of F5 Generation

1) Obtaining of F5 Generation

The selected F4 single plant grains obtained in the above 5 were simultaneously sown in rows and sowed in plots, to obtain F5 plant-to-row populations and F5 plot populations. The row was 4 meters long and 1.5 meters wide. The high-yield control (Jimai 22) and the high-quality control (Jinan 17) were planted at the same time.

2) Identification of F5 Generation

Single plants that met both selection criteria of plant-to-row populations and plots selection criteria were chosen as a target variety; specifically as follows:

A. Selection of Plots (1) Selection of Fields

The plots with the grade of winter freezing injury is less than or equal to 3, number of ears per mu greater than the high-quality control or equal to the high-yield control, and lodging less than or equal to grade 2 were chosen as field selection plots;

Lodging grade was based on the national standard for wheat variety test records: grade "1": no lodging; grade "2": slightly lodging, with a plant inclination angle of less than 30; grade "3": moderate lodging, with a plant inclination angle of 30-45; grade "4": serious lodging, with a plant inclination angle of 45-60; grade "5": serious lodging, with a plant inclination angle of more than 60.

The F5 plot populations derived from the combination of Ji 954072 and Jinan 17 had a winter freezing injury of grade 3, number of ears per mu of 440,000 (400,000 for high-quality control and 450,000 for high-yield control) and a lodging grade of 2.

(2) Quality Identification

The grains of F5 plot populations that met the field selection criteria were harvested to undergo determination of dough characteristics and bread processing quality using a farinograph (refer to ICC standard, No. 115 and *Wheat flour-Physical characteristics of doughs-Determination of water absorption and rheological properties using a farinograph*, GB/T14614-2006).

The F5 generation combination with the stability time of the dough properties not less than 8 minutes and the bread score not less than 80 were chosen.

The stability time of F5 plot populations derived from the combination of Ji 954072 and Jinan 17 was 40 minutes and the bread score was 89.5.

Therefore, the F5 plot populations derived from the combination of Ji 954072 and Jinan 17 were plot populations for quality identification.

(3) Yield Detection

The combinations with plot yield (calculated by the same method as before) greater than the high-quality control or greater than or equal to the high-yield control, below 5% lower than the high-yield control variety were chosen.

The yield of F5 plot populations derived from the combination of Ji 954072 and Jinan 17 was 5.28 kg; and the plot yield of high-quality control was 4.88 kg; the plot yield of high-yield control was 5.78 kg.

Therefore, the F5 plot populations derived from the combination of Ji 954072 and Jimai 19 met the above criteria and it was the selected F5 plot.

B. Plant-to-Row Selection (1) Detection of Plant-to-Row Yield

The whole row of F5 plant-to-row populations was harvested and the yield was counted.

The plant-to-rows with the yield greater than the high-quality control variety or greater than or equal to the high-yield control variety, or below 5% lower than the high-yield control variety were chosen.

The yields of plant-to-rows of F5 plant-to-row populations derived from the combination of Ji 954072 and Jinan 17 that met the above criteria were 11.3 kg, 10.85 kg, 12.51 kg, and 11.32 kg, respectively.

The plant-to-rows were chosen according to the above criteria, and recorded as selected plant-to-rows of F5 generation.

(2) Molecular Marker Detection of Plant-to-Rows

The above selected plant-to-rows of F5 generation were detected by Dx5 and By8 molecular markers respectively. The plant-to-rows containing 7+8 and 5+10 subunits (generally subunit 1 needed not to be identified because it was present in the original parents and progenies) were chosen.

The plant-to-rows of F5 generation derived from the combination of Ji 954072 and Jinan 17 contained 7+8 and 5+10 subunits, which were the selected plant-to-rows;

The F5 single plants derived from the combination of Ji 954072 and Jinan 17 that met the conditions for both plot identification and identification of plant-to-rows were selected, namely, the target variety, and it was named Jimai 44.

II. Detection of the New Wheat Variety Jimai 44

Figure 7:
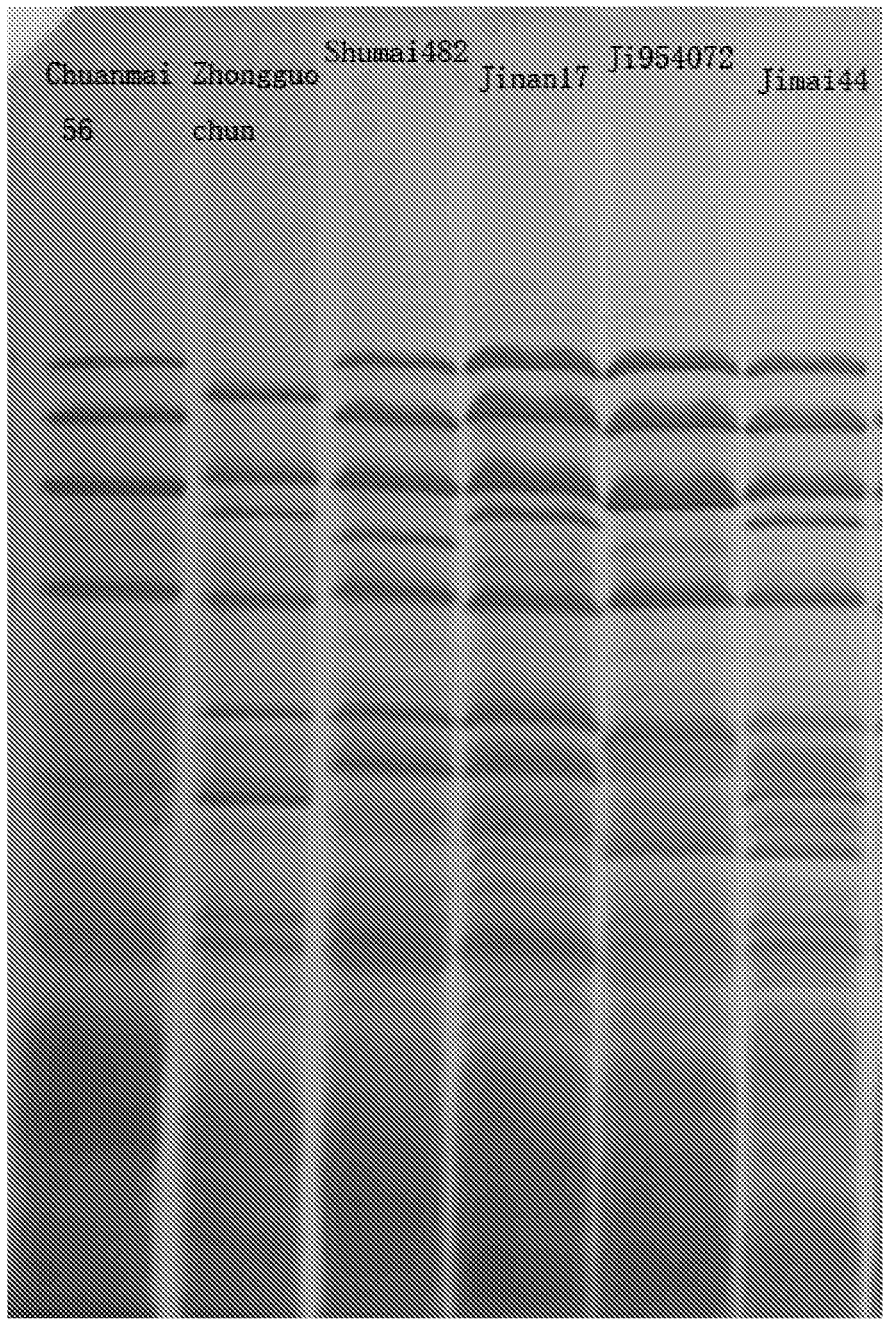
FIG. 7 shows HMW-GS SDS-PAGE electrophoresis patterns, from left to right: lane 1: Chuanmai 56 (standard control); lane 2: Zhongguochun (standard control); lane 3: Shumai 482 (standard control); lane 4: Jinan 17; lane 5: Ji 954072; lane 6: Jimai 44.

The new wheat variety Jimai 44 was taken out of the nursery for various regional trials. At present, it was participating in the second-year high-fertility regional trial of Shandong Province and national variety comparison trial. The variety has the characteristics of stable growth in the spring, raised flag leaves, compact plant type, good stalk elasticity and strong lodging resistance. The plant height is about 80 cm and it is an early maturity variety, and its maturity period is 2 to 3 days earlier than Jimai 22. It has the features of large ears, rectangular shape, long awn, white grain, horny and full grains. From 2014 to 2015, Jimai 44 participated in the preliminary test of Shandong Province, and the unified quality test results showed that, the grain protein content was 15.4%, dough stabilization time was 41.8 min, maximum extension resistance was 800 BU, which met the standard of national high-quality strong gluten wheat. From 2015 to 2016, Jimai 44 participated in the first year of regional trial in Shandong province, and the unified quality test results showed that the grain protein content was 14.7%, the dough stability time was 39.5 min, which met the standard of national high-quality strong gluten wheat. Compared with the control variety Jimai 22, its yield was increased by 2.3%. Its comprehensive characteristics were excellent, with very high promotion value. Molecular marker and SDS-PAGE detections showed that it contained 1, 7+8, and 5+10 subunits (FIG. 7, from left to right: lane 1: Chuanmai 56 (standard control); lane 2: Zhongguochun (standard control); lane 3: Shumai 482 (standard control); lane 4: Jinan 17; lane 5: Ji 954072; lane 6: Jimai 44).

What is claimed is:

1. A method for breeding a wheat plant (Plant A) comprising high-molecular-weight glutenin subunits (HMW-GS) 1 and 5+10 with a wheat plant (Plant B) comprising HMW-GS 1 and 7+8, the method comprising the following steps:
   A) hybridizing the Plant A with the Plant B to obtain F0 hybrid grains;
   B) hand sowing the F0 hybrid grains to obtain an F1 single-row population;
   C) selecting an F1 wheat plant in which yield per plant is greater than that of wheat plant Jinan 17 or greater than or equal to that of wheat plant Jimai 22, or is 5% or less lower than that of wheat plant Jimai 22;
   D) collecting seeds from the selected F1 plant;
   E) choosing seeds larger than 8-mesh sieve;
   F) plot sowing said seeds to obtain an F2 plot population;
   G) selecting an F2 plant from the F2 plot population that meets the following criteria i) to iii):
      i) said F2 plant has a stripe rust grade of less than 4 and a winter freezing injury grade of less than 4;
      ii) said F2 plant has a yield greater than that of the Jinan 17 or greater than or equal to that of the Jimai 22, or 5% or less lower than that of wheat plant Jimai 22; and
      iii) said F2 plant has a thousand grain weight (TGW) of greater than or equal to 35 g;
   H) hand sowing seeds of the selected F2 plant in the selected F2 plant to obtain an F3 population;
   I) selecting an F3 plant from the F3 population that meets the following criteria i) to iii):
      i) said F3 plant comprises HMW-GS glutenin subunits 1, 7+8 and 5+10;
      ii) said F3 plant comprises no less than 5 tiller-earing, stick or square ears, flag leaves raised, a powdery mildew grade of less than 4, a stripe rust grade of less than 4, and a plant height of 70-85 cm; and
      iii) the protein content of said F3 plant's grains is greater than or equal to 13% of the F3 plant's grain;
   J) hand sowing seeds of the selected F3 plant to obtain an F4 plant-to-row population;
   K) selecting an F4 plant from the F4 plant-to-row population that meets the following criteria i) to v):
      i) said F4 plant has a winter freezing injury of less than or equal to grade 3;
      ii) said F4 plant has a powdery mildew grade and a stripe rust grade of less than 4;
      iii) said F4 plant has a plant height of 75-80 cm; iv) said F4 plant has a TGW of greater than or equal to 38 g; and
      v) said F4 plant has a peak time of mixograph not less than 2 minutes;
   L) hand sowing seeds of the selected F4 plant to obtain an F5 plant-to-row population; or plot sowing seeds of the selected F4 plant to obtain an F5 plot population; and
   M) selecting an F5 plant from either the F5 plot population or the F5 plant-to-row population following criteria i) to ii):
      i) selecting an F5 plant from the F5 plot population that meets the following selection criteria (1) to (3): (1) said F5 plant has a winter freezing injury grade of less than or equal to 3, a number of ears per plot of about 600 $m^2$ greater than that of the Jinan 17 or equal to that of the Jimai 22, and a lodging grade of less than or equal to 2; (2) flour of said F5 plant has a dough stability time of not less than 8 minutes, and is scored at least eighty (80) percentile in sensory evaluations; and (3) said F5 plant has a plot yield greater than that of the Jinan 17 or greater than or equal to that of the Jimai 22, or less than 5% lower than the Jimai 22; or
      ii) selecting an F5 plant from the F5 plant-to-row population that meets the following selection criteria (1) to (2): (1) said F5 plant has a yield greater than that of the Jinan 17 or greater than or equal to that of the Jimai 22, or less than 5% lower than that of the Jimai 22; and (2) said F5 plant comprises HMW-GS 1, 7+8 and 5+10;
   wherein the Plant A is Ji954072 and the Plant B is Jinan 17 or Jimai 19.

2. The method of claim 1, wherein the plot sowing occurs by sowing in strips; or the hand sowing occurs by plant-to-row sowing.

* * * * *